(12) United States Patent
Kollar et al.

(10) Patent No.: US 11,197,676 B2
(45) Date of Patent: Dec. 14, 2021

(54) TIE-DOWN METHOD FOR ANVIL ASSEMBLY DELIVERY SYSTEM

(71) Applicant: Covidien LP, Mansfield, MA (US)

(72) Inventors: Charles Kollar, West Hartford, CT (US); Haley Strassner, Hamden, CT (US)

(73) Assignee: Covidien LP, Mansfield, MA (US)

( * ) Notice: Subject to any disclaimer, the term of this patent is extended or adjusted under 35 U.S.C. 154(b) by 105 days.

(21) Appl. No.: 16/414,014

(22) Filed: May 16, 2019

(65) Prior Publication Data

US 2020/0000474 A1    Jan. 2, 2020

Related U.S. Application Data

(60) Provisional application No. 62/690,995, filed on Jun. 28, 2018.

(51) Int. Cl.
*A61B 17/115*  (2006.01)
*A61B 17/04*   (2006.01)
*A61B 17/068*  (2006.01)
*A61B 17/072*  (2006.01)

(52) U.S. Cl.
CPC ........ *A61B 17/115* (2013.01); *A61B 17/0469* (2013.01); *A61B 17/068* (2013.01); *A61B 2017/07257* (2013.01)

(58) Field of Classification Search
CPC . A61B 17/0469; A61B 17/068; A61B 17/115; A61B 17/1155; A61B 2017/00477; A61B 2017/00292; A61B 2017/07257
See application file for complete search history.

(56) References Cited

U.S. PATENT DOCUMENTS

| | | |
|---|---|---|
| 3,193,165 A | 7/1965 | Akhalaya et al. |
| 3,388,847 A | 6/1968 | Kasulin et al. |
| 3,552,626 A | 1/1971 | Astafiev et al. |
| 3,638,652 A | 2/1972 | Kelley |
| 3,771,526 A | 11/1973 | Rudie |
| 4,198,982 A | 4/1980 | Fortner et al. |
| 4,207,898 A | 6/1980 | Becht |
| 4,289,133 A | 9/1981 | Rothfuss |
| 4,304,236 A | 12/1981 | Conta et al. |
| 4,319,576 A | 3/1982 | Rothfuss |
| 4,350,160 A | 9/1982 | Kolesov et al. |
| 4,351,466 A | 9/1982 | Noiles |

(Continued)

FOREIGN PATENT DOCUMENTS

| | | |
|---|---|---|
| CA | 908529 A | 8/1972 |
| CA | 2805365 A1 | 8/2013 |

(Continued)

OTHER PUBLICATIONS

European Search Report dated Sep. 17, 2019, issued in EP Appln. No. 19183027.

*Primary Examiner* — Andrew M Tecco
*Assistant Examiner* — Nicholas E Igbokwe
(74) *Attorney, Agent, or Firm* — Carter, DeLuca & Farrell LLP (57) ABSTRACT

A method of securing a head assembly of the anvil assembly in a delivery position for trans-oral delivery includes tying a suture such that lengths of suture extending between an adapter assembly and the head assembly are in contact with one another and/or are parallel.

18 Claims, 6 Drawing Sheets

(56) References Cited

U.S. PATENT DOCUMENTS

| | | |
|---|---|---|
| 4,379,457 A | 4/1983 | Gravener et al. |
| 4,473,077 A | 9/1984 | Noiles et al. |
| 4,476,863 A | 10/1984 | Kanshin et al. |
| 4,485,817 A | 12/1984 | Swiggett |
| 4,488,523 A | 12/1984 | Shichman |
| 4,505,272 A | 3/1985 | Utyamyshev et al. |
| 4,505,414 A | 3/1985 | Filipi |
| 4,520,817 A | 6/1985 | Green |
| 4,550,870 A | 11/1985 | Krumme et al. |
| 4,573,468 A | 3/1986 | Conta et al. |
| 4,576,167 A | 3/1986 | Noiles |
| 4,592,354 A | 6/1986 | Rothfuss |
| 4,603,693 A | 8/1986 | Conta et al. |
| 4,606,343 A | 8/1986 | Conta et al. |
| 4,632,290 A | 12/1986 | Green et al. |
| 4,646,745 A | 3/1987 | Noiles |
| 4,665,917 A | 5/1987 | Clanton et al. |
| 4,667,673 A | 5/1987 | Li |
| 4,671,445 A | 6/1987 | Barker et al. |
| 4,700,703 A | 10/1987 | Resnick et al. |
| 4,703,887 A | 11/1987 | Clanton et al. |
| 4,708,141 A | 11/1987 | Inoue et al. |
| 4,717,063 A | 1/1988 | Ebihara |
| 4,752,024 A | 6/1988 | Green et al. |
| 4,754,909 A | 7/1988 | Barker et al. |
| 4,776,506 A | 10/1988 | Green |
| 4,817,847 A | 4/1989 | Redtenbacher et al. |
| 4,873,977 A | 10/1989 | Avant et al. |
| 4,893,662 A | 1/1990 | Gervasi |
| 4,903,697 A | 2/1990 | Resnick et al. |
| 4,907,591 A | 3/1990 | Vasconcellos et al. |
| 4,917,114 A | 4/1990 | Green et al. |
| 4,957,499 A | 9/1990 | Lipatov et al. |
| 4,962,877 A | 10/1990 | Hervas |
| 5,005,749 A | 4/1991 | Aranyi |
| 5,042,707 A | 8/1991 | Taheri |
| 5,047,039 A | 9/1991 | Avant et al. |
| 5,104,025 A | 4/1992 | Main et al. |
| 5,119,983 A | 6/1992 | Green et al. |
| 5,122,156 A | 6/1992 | Granger et al. |
| 5,139,513 A | 8/1992 | Segato |
| 5,158,222 A | 10/1992 | Green et al. |
| 5,188,638 A | 2/1993 | Tzakis |
| 5,193,731 A | 3/1993 | Aranyi |
| 5,197,648 A | 3/1993 | Gingold |
| 5,197,649 A | 3/1993 | Bessler et al. |
| 5,205,459 A | 4/1993 | Brinkerhoff et al. |
| 5,221,036 A | 6/1993 | Takase |
| 5,222,963 A | 6/1993 | Brinkerhoff et al. |
| 5,253,793 A | 10/1993 | Green et al. |
| 5,261,920 A | 11/1993 | Main et al. |
| 5,271,543 A | 12/1993 | Grant et al. |
| 5,271,544 A | 12/1993 | Fox et al. |
| 5,275,322 A | 1/1994 | Brinkerhoff et al. |
| 5,282,810 A | 2/1994 | Allen et al. |
| 5,285,944 A | 2/1994 | Green et al. |
| 5,285,945 A | 2/1994 | Brinkerhoff et al. |
| 5,292,053 A | 3/1994 | Bilotti et al. |
| 5,309,927 A | 5/1994 | Welch |
| 5,312,024 A | 5/1994 | Grant et al. |
| 5,314,435 A | 5/1994 | Green et al. |
| 5,314,436 A | 5/1994 | Wilk |
| 5,330,486 A | 7/1994 | Wilk |
| 5,333,773 A | 8/1994 | Main et al. |
| 5,344,059 A | 9/1994 | Green et al. |
| 5,346,115 A | 9/1994 | Perouse et al. |
| 5,348,259 A | 9/1994 | Blanco et al. |
| 5,350,104 A | 9/1994 | Main et al. |
| 5,355,897 A | 10/1994 | Pietrafitta et al. |
| 5,360,154 A | 11/1994 | Green |
| 5,368,215 A | 11/1994 | Green et al. |
| 5,392,979 A | 2/1995 | Green et al. |
| 5,395,030 A | 3/1995 | Kuramoto et al. |
| 5,403,333 A | 4/1995 | Kaster et al. |
| 5,404,870 A | 4/1995 | Brinkerhoff et al. |
| 5,411,508 A | 5/1995 | Bessler et al. |
| 5,425,738 A | 6/1995 | Gustafson et al. |
| 5,433,721 A | 7/1995 | Hooven et al. |
| 5,437,684 A | 8/1995 | Calabrese et al. |
| 5,439,156 A | 8/1995 | Grant et al. |
| 5,443,198 A | 8/1995 | Viola et al. |
| 5,447,514 A | 9/1995 | Gerry et al. |
| 5,454,825 A | 10/1995 | Van Leeuwen et al. |
| 5,464,415 A | 11/1995 | Chen |
| 5,470,006 A | 11/1995 | Rodak |
| 5,474,223 A | 12/1995 | Viola et al. |
| 5,497,934 A | 3/1996 | Brady et al. |
| 5,503,635 A | 4/1996 | Sauer et al. |
| 5,522,534 A | 6/1996 | Viola et al. |
| 5,533,661 A | 7/1996 | Main et al. |
| 5,588,579 A | 12/1996 | Schnut et al. |
| 5,609,285 A | 3/1997 | Grant et al. |
| 5,626,591 A | 5/1997 | Kockerling et al. |
| 5,632,433 A | 5/1997 | Grant et al. |
| 5,639,008 A | 6/1997 | Gallagher et al. |
| 5,641,111 A | 6/1997 | Ahrens et al. |
| 5,658,300 A | 8/1997 | Bito et al. |
| 5,669,918 A | 9/1997 | Balazs et al. |
| 5,685,474 A | 11/1997 | Seeber |
| 5,709,335 A | 1/1998 | Heck |
| 5,715,987 A | 2/1998 | Kelley et al. |
| 5,718,360 A | 2/1998 | Green et al. |
| 5,720,755 A | 2/1998 | Dakov |
| 5,732,872 A | 3/1998 | Bolduc et al. |
| 5,749,896 A | 5/1998 | Cook |
| 5,758,814 A | 6/1998 | Gallagher et al. |
| 5,799,857 A | 9/1998 | Robertson et al. |
| 5,814,055 A | 9/1998 | Knodel et al. |
| 5,833,698 A | 11/1998 | Hinchliffe et al. |
| 5,836,503 A | 11/1998 | Ehrenfels et al. |
| 5,839,639 A | 11/1998 | Sauer et al. |
| 5,855,312 A | 1/1999 | Toledano |
| 5,860,581 A | 1/1999 | Robertson et al. |
| 5,868,760 A | 2/1999 | McGuckin, Jr. |
| 5,881,943 A | 3/1999 | Heck et al. |
| 5,915,616 A | 6/1999 | Viola et al. |
| 5,947,363 A | 9/1999 | Bolduc et al. |
| 5,951,576 A | 9/1999 | Wakabayashi |
| 5,957,363 A | 9/1999 | Heck |
| 5,993,468 A | 11/1999 | Rygaard |
| 6,024,748 A | 2/2000 | Manzo et al. |
| 6,050,472 A | 4/2000 | Shibata |
| 6,053,390 A | 4/2000 | Green et al. |
| 6,068,636 A | 5/2000 | Chen |
| 6,083,241 A | 7/2000 | Longo et al. |
| 6,102,271 A | 8/2000 | Longo et al. |
| 6,117,148 A | 9/2000 | Ravo et al. |
| 6,119,913 A | 9/2000 | Adams et al. |
| 6,126,058 A | 10/2000 | Adams et al. |
| 6,142,933 A | 11/2000 | Longo et al. |
| 6,149,667 A | 11/2000 | Hovland et al. |
| 6,176,413 B1 | 1/2001 | Heck et al. |
| 6,179,195 B1 | 1/2001 | Adams et al. |
| 6,193,129 B1 | 2/2001 | Bittner et al. |
| 6,203,553 B1 | 3/2001 | Robertson et al. |
| 6,209,773 B1 | 4/2001 | Bolduc et al. |
| 6,241,140 B1 | 6/2001 | Adams et al. |
| 6,253,984 B1 | 7/2001 | Heck et al. |
| 6,258,107 B1 | 7/2001 | Balazs et al. |
| 6,264,086 B1 | 7/2001 | McGuckin, Jr. |
| 6,269,997 B1 | 8/2001 | Balazs et al. |
| 6,273,897 B1 | 8/2001 | Dalessandro et al. |
| 6,279,809 B1 | 8/2001 | Nicolo |
| 6,302,311 B1 | 10/2001 | Adams et al. |
| 6,338,737 B1 | 1/2002 | Toledano |
| 6,343,731 B1 | 2/2002 | Adams et al. |
| 6,387,105 B1 | 5/2002 | Gifford, III et al. |
| 6,398,795 B1 | 6/2002 | McAlister et al. |
| 6,402,008 B1 | 6/2002 | Lucas |
| 6,439,446 B1 | 8/2002 | Perry et al. |
| 6,443,973 B1 | 9/2002 | Whitman |
| 6,450,390 B2 | 9/2002 | Heck et al. |
| 6,478,210 B2 | 11/2002 | Adams et al. |
| 6,488,197 B1 | 12/2002 | Whitman |

(56) References Cited

U.S. PATENT DOCUMENTS

| | | |
|---|---|---|
| 6,491,201 B1 | 12/2002 | Whitman |
| 6,494,877 B2 | 12/2002 | Odell et al. |
| 6,503,259 B2 | 1/2003 | Huxel et al. |
| 6,517,566 B1 | 2/2003 | Hovland et al. |
| 6,520,398 B2 | 2/2003 | Nicolo |
| 6,533,157 B1 | 3/2003 | Whitman |
| 6,551,334 B2 | 4/2003 | Blatter et al. |
| 6,578,751 B2 | 6/2003 | Hartwick |
| 6,585,144 B2 | 7/2003 | Adams et al. |
| 6,588,643 B2 | 7/2003 | Bolduc et al. |
| 6,592,596 B1 | 7/2003 | Geitz |
| 6,601,749 B2 | 8/2003 | Sullivan et al. |
| 6,605,078 B2 | 8/2003 | Adams |
| 6,605,098 B2 | 8/2003 | Nobis et al. |
| 6,626,921 B2 | 9/2003 | Blatter et al. |
| 6,629,630 B2 | 10/2003 | Adams |
| 6,631,837 B1 | 10/2003 | Heck |
| 6,632,227 B2 | 10/2003 | Adams |
| 6,632,237 B2 | 10/2003 | Ben-David et al. |
| 6,652,542 B2 | 11/2003 | Blatter et al. |
| 6,659,327 B2 | 12/2003 | Heck et al. |
| 6,676,671 B2 | 1/2004 | Robertson et al. |
| 6,681,979 B2 | 1/2004 | Whitman |
| 6,685,079 B2 | 2/2004 | Sharma et al. |
| 6,695,198 B2 | 2/2004 | Adams et al. |
| 6,695,199 B2 | 2/2004 | Whitman |
| 6,698,643 B2 | 3/2004 | Whitman |
| 6,716,222 B2 | 4/2004 | McAlister et al. |
| 6,716,233 B1 | 4/2004 | Whitman |
| 6,726,697 B2 | 4/2004 | Nicholas et al. |
| 6,742,692 B2 | 6/2004 | Hartwick |
| 6,743,244 B2 | 6/2004 | Blatter et al. |
| 6,763,993 B2 | 7/2004 | Bolduc et al. |
| 6,769,590 B2 | 8/2004 | Vresh et al. |
| 6,769,594 B2 | 8/2004 | Orban, III |
| 6,820,791 B2 | 11/2004 | Adams |
| 6,821,282 B2 | 11/2004 | Perry et al. |
| 6,827,246 B2 | 12/2004 | Sullivan et al. |
| 6,840,423 B2 | 1/2005 | Adams et al. |
| 6,843,403 B2 | 1/2005 | Whitman |
| 6,846,308 B2 | 1/2005 | Whitman et al. |
| 6,852,122 B2 | 2/2005 | Rush |
| 6,866,178 B2 | 3/2005 | Adams et al. |
| 6,872,214 B2 | 3/2005 | Sonnenschein et al. |
| 6,874,669 B2 | 4/2005 | Adams et al. |
| 6,884,250 B2 | 4/2005 | Monassevitch et al. |
| 6,905,504 B1 | 6/2005 | Vargas |
| 6,938,814 B2 | 9/2005 | Sharma et al. |
| 6,942,675 B1 | 9/2005 | Vargas |
| 6,945,444 B2 | 9/2005 | Gresham et al. |
| 6,953,138 B1 | 10/2005 | Dworak et al. |
| 6,957,758 B2 | 10/2005 | Aranyi |
| 6,959,851 B2 | 11/2005 | Heinrich |
| 6,978,922 B2 | 12/2005 | Bilotti et al. |
| 6,981,941 B2 | 1/2006 | Whitman et al. |
| 6,981,979 B2 | 1/2006 | Nicolo |
| 7,032,798 B2 | 4/2006 | Whitman et al. |
| 7,059,331 B2 | 6/2006 | Adams et al. |
| 7,059,510 B2 | 6/2006 | Orban, III |
| 7,077,856 B2 | 7/2006 | Whitman |
| 7,080,769 B2 | 7/2006 | Vresh et al. |
| 7,086,267 B2 | 8/2006 | Dworak et al. |
| 7,114,642 B2 | 10/2006 | Whitman |
| 7,118,528 B1 | 10/2006 | Piskun |
| 7,122,044 B2 | 10/2006 | Bolduc et al. |
| 7,128,748 B2 | 10/2006 | Mooradian et al. |
| 7,141,055 B2 | 11/2006 | Abrams et al. |
| 7,168,604 B2 | 1/2007 | Milliman et al. |
| 7,179,267 B2 | 2/2007 | Nolan et al. |
| 7,182,239 B1 | 2/2007 | Myers |
| 7,195,142 B2 | 3/2007 | Orban, III |
| 7,207,168 B2 | 4/2007 | Doepker et al. |
| 7,220,237 B2 | 5/2007 | Gannoe et al. |
| 7,234,624 B2 | 6/2007 | Gresham et al. |
| 7,235,089 B1 | 6/2007 | McGuckin, Jr. |
| RE39,841 E | 9/2007 | Bilotti et al. |
| 7,285,125 B2 | 10/2007 | Viola |
| 7,303,106 B2 | 12/2007 | Milliman et al. |
| 7,303,107 B2 | 12/2007 | Milliman et al. |
| 7,309,341 B2 | 12/2007 | Ortiz et al. |
| 7,322,994 B2 | 1/2008 | Nicholas et al. |
| 7,325,713 B2 | 2/2008 | Aranyi |
| 7,334,718 B2 | 2/2008 | McAlister et al. |
| 7,335,212 B2 | 2/2008 | Edoga et al. |
| 7,364,060 B2 | 4/2008 | Milliman |
| 7,398,908 B2 | 7/2008 | Holsten et al. |
| 7,399,305 B2 | 7/2008 | Csiky et al. |
| 7,401,721 B2 | 7/2008 | Holsten et al. |
| 7,401,722 B2 | 7/2008 | Hur |
| 7,407,075 B2 | 8/2008 | Holsten et al. |
| 7,410,086 B2 | 8/2008 | Ortiz et al. |
| 7,422,137 B2 | 9/2008 | Manzo |
| 7,422,138 B2 | 9/2008 | Bilotti et al. |
| 7,431,191 B2 | 10/2008 | Milliman |
| 7,438,718 B2 | 10/2008 | Milliman et al. |
| 7,455,676 B2 | 11/2008 | Holsten et al. |
| 7,455,682 B2 | 11/2008 | Viola |
| 7,481,347 B2 | 1/2009 | Roy |
| 7,494,038 B2 | 2/2009 | Milliman |
| 7,506,791 B2 | 3/2009 | Omaits et al. |
| 7,516,877 B2 | 4/2009 | Aranyi |
| 7,527,185 B2 | 5/2009 | Harari et al. |
| 7,537,602 B2 | 5/2009 | Whitman |
| 7,540,839 B2 | 6/2009 | Butler et al. |
| 7,546,939 B2 | 6/2009 | Adams et al. |
| 7,546,940 B2 | 6/2009 | Milliman et al. |
| 7,547,312 B2 | 6/2009 | Bauman et al. |
| 7,556,186 B2 | 7/2009 | Milliman |
| 7,559,451 B2 | 7/2009 | Sharma et al. |
| 7,585,306 B2 | 9/2009 | Abbott et al. |
| 7,588,174 B2 | 9/2009 | Holsten et al. |
| 7,600,663 B2 | 10/2009 | Green |
| 7,611,038 B2 | 11/2009 | Racenet et al. |
| 7,635,385 B2 | 12/2009 | Milliman et al. |
| 7,669,747 B2 | 3/2010 | Weisenburgh, II et al. |
| 7,686,201 B2 | 3/2010 | Csiky |
| 7,694,864 B2 | 4/2010 | Okada et al. |
| 7,699,204 B2 | 4/2010 | Viola |
| 7,708,181 B2 | 5/2010 | Cole et al. |
| 7,717,313 B2 | 5/2010 | Criscuolo et al. |
| 7,721,932 B2 | 5/2010 | Cole et al. |
| 7,726,539 B2 | 6/2010 | Holsten et al. |
| 7,743,958 B2 | 6/2010 | Orban, III |
| 7,744,627 B2 | 6/2010 | Orban, III et al. |
| 7,770,776 B2 | 8/2010 | Chen et al. |
| 7,771,440 B2 | 8/2010 | Ortiz et al. |
| 7,776,060 B2 | 8/2010 | Mooradian et al. |
| 7,793,813 B2 | 9/2010 | Bettuchi |
| 7,802,712 B2 | 9/2010 | Milliman et al. |
| 7,823,592 B2 | 11/2010 | Bettuchi et al. |
| 7,837,079 B2 | 11/2010 | Holsten et al. |
| 7,837,080 B2 | 11/2010 | Schwemberger |
| 7,837,081 B2 | 11/2010 | Holsten et al. |
| 7,845,536 B2 | 12/2010 | Viola et al. |
| 7,845,538 B2 | 12/2010 | Whitman |
| 7,857,187 B2 | 12/2010 | Milliman |
| 7,886,951 B2 | 2/2011 | Hessler |
| 7,896,215 B2 | 3/2011 | Adams et al. |
| 7,900,806 B2 | 3/2011 | Chen et al. |
| 7,909,039 B2 | 3/2011 | Hur |
| 7,909,219 B2 | 3/2011 | Cole et al. |
| 7,909,222 B2 | 3/2011 | Cole et al. |
| 7,909,223 B2 | 3/2011 | Cole et al. |
| 7,913,892 B2 | 3/2011 | Cole et al. |
| 7,918,377 B2 | 4/2011 | Measamer et al. |
| 7,922,062 B2 | 4/2011 | Cole et al. |
| 7,922,743 B2 | 4/2011 | Heinrich et al. |
| 7,931,183 B2 | 4/2011 | Orban, III |
| 7,938,307 B2 | 5/2011 | Bettuchi |
| 7,942,302 B2 | 5/2011 | Roby et al. |
| 7,951,166 B2 | 5/2011 | Orban, III et al. |
| 7,959,050 B2 | 6/2011 | Smith et al. |
| 7,967,181 B2 | 6/2011 | Viola et al. |
| 7,975,895 B2 | 7/2011 | Milliman |

(56) References Cited

U.S. PATENT DOCUMENTS

| | | |
|---|---|---|
| 8,002,795 B2 | 8/2011 | Beetel |
| 8,006,701 B2 | 8/2011 | Bilotti et al. |
| 8,006,889 B2 | 8/2011 | Adams et al. |
| 8,011,551 B2 | 9/2011 | Marczyk et al. |
| 8,011,554 B2 | 9/2011 | Milliman |
| 8,016,177 B2 | 9/2011 | Bettuchi et al. |
| 8,016,858 B2 | 9/2011 | Whitman |
| 8,020,741 B2 | 9/2011 | Cole et al. |
| 8,025,199 B2 | 9/2011 | Whitman et al. |
| 8,028,885 B2 | 10/2011 | Smith et al. |
| 8,038,046 B2 | 10/2011 | Smith et al. |
| 8,043,207 B2 | 10/2011 | Adams |
| 8,066,167 B2 | 11/2011 | Measamer et al. |
| 8,066,169 B2 | 11/2011 | Viola |
| 8,070,035 B2 | 12/2011 | Holsten et al. |
| 8,070,037 B2 | 12/2011 | Csiky |
| 8,096,458 B2 | 1/2012 | Hessler |
| 8,109,426 B2 | 2/2012 | Milliman et al. |
| 8,109,427 B2 | 2/2012 | Orban, III |
| 8,113,405 B2 | 2/2012 | Milliman |
| 8,113,406 B2 | 2/2012 | Holsten et al. |
| 8,113,407 B2 | 2/2012 | Holsten et al. |
| 8,123,103 B2 | 2/2012 | Milliman |
| 8,128,645 B2 | 3/2012 | Sonnenschein et al. |
| 8,132,703 B2 | 3/2012 | Milliman et al. |
| 8,136,712 B2 | 3/2012 | Zingman |
| 8,146,790 B2 | 4/2012 | Milliman |
| 8,146,791 B2 | 4/2012 | Bettuchi et al. |
| 8,181,838 B2 | 5/2012 | Milliman et al. |
| 8,192,460 B2 | 6/2012 | Orban, III et al. |
| 8,201,720 B2 | 6/2012 | Hessler |
| 8,203,782 B2 | 6/2012 | Brueck et al. |
| 8,211,130 B2 | 7/2012 | Viola |
| 8,225,799 B2 | 7/2012 | Bettuchi |
| 8,225,981 B2 | 7/2012 | Criscuolo et al. |
| 8,231,041 B2 | 7/2012 | Marczyk et al. |
| 8,231,042 B2 | 7/2012 | Hessler et al. |
| 8,257,391 B2 | 9/2012 | Orban, III et al. |
| 8,267,301 B2 | 9/2012 | Milliman et al. |
| 8,272,552 B2 | 9/2012 | Holsten et al. |
| 8,276,802 B2 | 10/2012 | Kostrzewski |
| 8,281,975 B2 | 10/2012 | Criscuolo et al. |
| 8,286,845 B2 | 10/2012 | Perry et al. |
| 8,308,045 B2 | 11/2012 | Bettuchi et al. |
| 8,312,885 B2 | 11/2012 | Bettuchi et al. |
| 8,313,014 B2 | 11/2012 | Bettuchi |
| 8,317,073 B2 | 11/2012 | Milliman et al. |
| 8,317,074 B2 | 11/2012 | Ortiz et al. |
| 8,322,590 B2 | 12/2012 | Patel et al. |
| 8,328,060 B2 | 12/2012 | Jankowski et al. |
| 8,328,062 B2 | 12/2012 | Viola |
| 8,328,063 B2 | 12/2012 | Milliman et al. |
| 8,343,185 B2 | 1/2013 | Milliman et al. |
| 8,353,438 B2 | 1/2013 | Baxter, III et al. |
| 8,353,439 B2 | 1/2013 | Baxter, III et al. |
| 8,353,930 B2 | 1/2013 | Heinrich et al. |
| 8,360,295 B2 | 1/2013 | Milliman et al. |
| 8,365,974 B2 | 2/2013 | Milliman |
| 8,403,942 B2 | 3/2013 | Milliman et al. |
| 8,408,441 B2 | 4/2013 | Wenchell et al. |
| 8,413,870 B2 | 4/2013 | Pastorelli et al. |
| 8,413,872 B2 | 4/2013 | Patel |
| 8,418,905 B2 | 4/2013 | Milliman |
| 8,418,909 B2 | 4/2013 | Kostrzewski |
| 8,424,535 B2 | 4/2013 | Hessler et al. |
| 8,424,741 B2 | 4/2013 | McGuckin, Jr. et al. |
| 8,430,291 B2 | 4/2013 | Heinrich et al. |
| 8,430,292 B2 | 4/2013 | Patel et al. |
| 8,453,910 B2 | 6/2013 | Bettuchi et al. |
| 8,453,911 B2 | 6/2013 | Milliman et al. |
| 8,485,414 B2 | 7/2013 | Criscuolo et al. |
| 8,490,853 B2 | 7/2013 | Criscuolo et al. |
| 8,511,533 B2 | 8/2013 | Viola et al. |
| 8,551,138 B2 | 10/2013 | Orban, III et al. |
| 8,567,655 B2 | 10/2013 | Nalagatla et al. |
| 8,579,178 B2 | 11/2013 | Holsten et al. |
| 8,590,763 B2 | 11/2013 | Milliman |
| 8,590,764 B2 | 11/2013 | Hartwick et al. |
| 8,608,047 B2 | 12/2013 | Holsten et al. |
| 8,616,428 B2 | 12/2013 | Milliman et al. |
| 8,616,429 B2 | 12/2013 | Viola |
| 8,622,275 B2 | 1/2014 | Baxter, III et al. |
| 8,631,993 B2 | 1/2014 | Kostrzewski |
| 8,636,187 B2 | 1/2014 | Hueil et al. |
| 8,640,940 B2 | 2/2014 | Ohdaira |
| 8,662,370 B2 | 3/2014 | Takei |
| 8,663,258 B2 | 3/2014 | Bettuchi et al. |
| 8,672,931 B2 | 3/2014 | Goldboss et al. |
| 8,678,264 B2 | 3/2014 | Racenet et al. |
| 8,684,248 B2 | 4/2014 | Milliman |
| 8,684,250 B2 | 4/2014 | Bettuchi et al. |
| 8,684,251 B2 | 4/2014 | Rebuffat et al. |
| 8,684,252 B2 | 4/2014 | Patel et al. |
| 8,733,611 B2 | 5/2014 | Milliman |
| 9,554,802 B2 | 1/2017 | Williams et al. |
| 9,861,367 B2 | 1/2018 | Williams |
| 2003/0111507 A1 | 6/2003 | Nunez |
| 2004/0073090 A1 | 4/2004 | Butler et al. |
| 2005/0051597 A1 | 3/2005 | Toledano |
| 2005/0107813 A1 | 5/2005 | Gilete Garcia |
| 2006/0000869 A1 | 1/2006 | Fontayne |
| 2006/0011698 A1 | 1/2006 | Okada et al. |
| 2006/0201989 A1 | 9/2006 | Ojeda |
| 2007/0027473 A1 | 2/2007 | Vresh et al. |
| 2007/0029363 A1 | 2/2007 | Popov |
| 2007/0060952 A1 | 3/2007 | Roby et al. |
| 2009/0236392 A1 | 9/2009 | Cole et al. |
| 2009/0236398 A1 | 9/2009 | Cole et al. |
| 2009/0236401 A1 | 9/2009 | Cole et al. |
| 2010/0019016 A1 | 1/2010 | Edoga et al. |
| 2010/0038401 A1* | 2/2010 | Milliman ............. A61B 17/068 227/175.1 |
| 2010/0051668 A1 | 3/2010 | Milliman et al. |
| 2010/0084453 A1 | 4/2010 | Hu |
| 2010/0147923 A1 | 6/2010 | D'Agostino et al. |
| 2010/0163598 A1 | 7/2010 | Belzer |
| 2010/0224668 A1 | 9/2010 | Fontayne et al. |
| 2010/0230465 A1 | 9/2010 | Smith et al. |
| 2010/0258611 A1 | 10/2010 | Smith et al. |
| 2010/0264195 A1 | 10/2010 | Bettuchi |
| 2010/0327041 A1 | 12/2010 | Milliman et al. |
| 2011/0011916 A1 | 1/2011 | Levine |
| 2011/0114697 A1 | 5/2011 | Baxter, III et al. |
| 2011/0114700 A1 | 5/2011 | Baxter, III et al. |
| 2011/0144640 A1 | 6/2011 | Heinrich et al. |
| 2011/0147432 A1 | 6/2011 | Heinrich et al. |
| 2011/0192882 A1 | 8/2011 | Hess et al. |
| 2012/0145755 A1 | 6/2012 | Kahn |
| 2012/0193395 A1 | 8/2012 | Pastorelli et al. |
| 2012/0193398 A1 | 8/2012 | Williams et al. |
| 2012/0232339 A1 | 9/2012 | Csiky |
| 2012/0273548 A1 | 11/2012 | Ma et al. |
| 2012/0325888 A1 | 12/2012 | Qiao et al. |
| 2013/0015232 A1 | 1/2013 | Smith et al. |
| 2013/0020372 A1 | 1/2013 | Jankowski et al. |
| 2013/0020373 A1 | 1/2013 | Smith et al. |
| 2013/0032628 A1 | 2/2013 | Li et al. |
| 2013/0056516 A1 | 3/2013 | Viola |
| 2013/0060258 A1 | 3/2013 | Giacomantonio |
| 2013/0105544 A1 | 5/2013 | Mozdzierz et al. |
| 2013/0105546 A1 | 5/2013 | Milliman et al. |
| 2013/0105551 A1 | 5/2013 | Zingman |
| 2013/0126580 A1 | 5/2013 | Smith et al. |
| 2013/0153630 A1 | 6/2013 | Miller et al. |
| 2013/0153631 A1 | 6/2013 | Vasudevan et al. |
| 2013/0153633 A1 | 6/2013 | Casasanta, Jr. et al. |
| 2013/0153634 A1 | 6/2013 | Carter et al. |
| 2013/0153638 A1 | 6/2013 | Carter et al. |
| 2013/0153639 A1 | 6/2013 | Hodgkinson et al. |
| 2013/0175315 A1 | 7/2013 | Milliman |
| 2013/0175318 A1 | 7/2013 | Felder et al. |
| 2013/0175319 A1 | 7/2013 | Felder et al. |
| 2013/0175320 A1 | 7/2013 | Mandakolathur Vasudevan et al. |
| 2013/0181035 A1 | 7/2013 | Milliman |

(56) References Cited

U.S. PATENT DOCUMENTS

| | | |
|---|---|---|
| 2013/0181036 A1 | 7/2013 | Olson et al. |
| 2013/0186930 A1 | 7/2013 | Wenchell et al. |
| 2013/0193185 A1 | 8/2013 | Patel |
| 2013/0193187 A1 | 8/2013 | Milliman |
| 2013/0193190 A1 | 8/2013 | Carter et al. |
| 2013/0193191 A1 | 8/2013 | Stevenson et al. |
| 2013/0193192 A1 | 8/2013 | Casasanta, Jr. et al. |
| 2013/0200131 A1 | 8/2013 | Racenet et al. |
| 2013/0206816 A1 | 8/2013 | Penna |
| 2013/0214027 A1 | 8/2013 | Hessler et al. |
| 2013/0214028 A1 | 8/2013 | Patel et al. |
| 2013/0228609 A1 | 9/2013 | Kostrzewski |
| 2013/0240597 A1 | 9/2013 | Milliman et al. |
| 2013/0240600 A1 | 9/2013 | Bettuchi |
| 2013/0248581 A1 | 9/2013 | Smith et al. |
| 2013/0277411 A1 | 10/2013 | Hodgkinson et al. |
| 2013/0277412 A1 | 10/2013 | Gresham et al. |
| 2013/0284792 A1 | 10/2013 | Ma |
| 2013/0292449 A1 | 11/2013 | Bettuchi et al. |
| 2013/0299553 A1 | 11/2013 | Mozdzierz |
| 2013/0299554 A1 | 11/2013 | Mozdzierz |
| 2013/0306701 A1 | 11/2013 | Olson |
| 2013/0306707 A1 | 11/2013 | Viola et al. |
| 2014/0008413 A1 | 1/2014 | Williams |
| 2014/0012317 A1 | 1/2014 | Orban et al. |
| 2014/0367444 A1* | 12/2014 | Williams ......... A61B 17/07207 227/175.1 |
| 2015/0129636 A1* | 5/2015 | Mulreed .............. A61B 17/115 227/177.1 |
| 2015/0366562 A1* | 12/2015 | Williams ............. A61B 17/064 227/175.1 |
| 2015/0366563 A1* | 12/2015 | Williams ........... A61B 17/1155 227/175.1 |
| 2016/0143641 A1 | 5/2016 | Sapienza et al. |
| 2016/0157855 A1* | 6/2016 | Williams ........... A61B 17/1155 227/180.1 |
| 2016/0157856 A1 | 6/2016 | Williams et al. |
| 2016/0174988 A1 | 6/2016 | D'Agostino et al. |
| 2016/0302792 A1 | 10/2016 | Motai |
| 2017/0000475 A1* | 1/2017 | Sgroi, Jr. ........... A61B 17/1155 |

FOREIGN PATENT DOCUMENTS

| | | |
|---|---|---|
| DE | 1057729 B | 5/1959 |
| DE | 3301713 A1 | 7/1984 |
| EP | 0152382 A2 | 8/1985 |
| EP | 0173451 A1 | 3/1986 |
| EP | 0190022 A2 | 8/1986 |
| EP | 0282157 A1 | 9/1988 |
| EP | 0503689 A2 | 9/1992 |
| EP | 1354560 A2 | 10/2003 |
| EP | 2042108 A2 | 4/2009 |
| EP | 2138118 A2 | 12/2009 |
| EP | 2168510 A1 | 3/2010 |
| EP | 2238926 A2 | 10/2010 |
| EP | 2524656 A2 | 11/2012 |
| EP | 2873380 A1 | 5/2015 |
| EP | 3120785 A1 | 1/2017 |
| FR | 1136020 A | 5/1957 |
| FR | 1461464 A | 2/1966 |
| FR | 1588250 A | 4/1970 |
| FR | 2443239 A1 | 7/1980 |
| GB | 1185292 A | 3/1970 |
| GB | 2016991 A | 9/1979 |
| GB | 2070499 A | 9/1981 |
| JP | 2004147969 A | 5/2004 |
| JP | 2013138860 A | 7/2013 |
| NL | 7711347 A | 4/1979 |
| SU | 1509052 A1 | 9/1989 |
| WO | 8706448 A1 | 11/1987 |
| WO | 8900406 A1 | 1/1989 |
| WO | 9006085 A1 | 6/1990 |
| WO | 98/35614 A1 | 8/1998 |
| WO | 0154594 A1 | 8/2001 |
| WO | 2008107918 A1 | 9/2008 |

\* cited by examiner

TIE-DOWN METHOD FOR ANVIL ASSEMBLY DELIVERY SYSTEM

CROSS-REFERENCE TO RELATED APPLICATIONS

This application claims the benefit of and priority to U.S. Provisional Patent Application No. 62/690,995 filed Jun. 28, 2018, the entire disclosure of which is incorporated by reference herein.

BACKGROUND

Technical Field

The present disclosure relates to delivery systems for trans-oral delivery of anvil assemblies into a body cavity of a patient. More particularly, the present disclosure relates to a tie-down method for securing an anvil assembly to a delivery system with the head assembly in a position for trans-oral delivery into a body cavity.

Background of Related Art

Trans-oral delivery systems for delivering an anvil assembly to a surgical site, e.g., the stomach, typically include a retaining suture for maintaining a head assembly of the anvil assembly in a position to facilitate atraumatic trans-oral insertion. Generally, the retaining suture extends between the head assembly of the anvil assembly and the delivery system to secure the anvil assembly to the delivery system with the head assembly in a tilted position. Once the anvil assembly has been positioned within the patient, the retaining suture is cut or otherwise released to permit the head assembly to pivot to an operative position.

Improved methods for tying-down a head assembly of an anvil assembly are desirable.

SUMMARY

An anvil delivery system is provided. The anvil delivery system includes a delivery assembly including an adapter member, an anvil assembly, and a suture. The adapter member defines a through bore. The anvil assembly includes a center rod assembly selectively securable to the adapter member, and a head assembly pivotally secured to the center rod assembly. The head assembly is pivotable between a first tilted position and an operative position, the head assembly including a housing have a first opening. The suture retains the head assembly in the first tilted position. The suture has first and second end portions. The suture extends through the through bore in the adapter member and includes a first knot securing the suture about the adapter member. The first and second end portions of the suture are received through the opening in the housing.

In embodiments, the housing further defines a pair of openings having first and second openings. The first end portion of the suture may be received through the first opening of the pair of openings and the second end portion of the suture may be received through the second opening of the pair of openings. The first and second end portions of the suture may form a second knot external of the first and second openings. First and second lengths of the suture may extend between the adapter member and the housing are in contact with one another and/or parallel with one another.

The delivery system may further include a flexible tube. The adapter assembly may be secured to the flexible tube. The head assembly may be movable to a second tilted position opposite the first tilted position.

Also provided is a method of securing an anvil assembly in a first tilted position. The method includes receiving a suture through a through bore of an adapter member of an anvil delivery system, securing the suture to the adapter member by tying a first knot in the suture, passing first and second ends of the suture through an opening in a housing of a head assembly of an anvil assembly, passing the first end of the suture through a first opening in the housing and passing the second end of the suture through a second opening in the housing, and securing the first and second ends of the suture together by tying a second knot in the suture adjacent the first and second ends of the suture to secure the head assembly in the first tilted position.

In embodiment, the method further includes moving the head assembly relative to a center rod assembly of the anvil assembly to the first tilted position prior to tying the second knot. The method may include securing the adapter member to a center rod assembly of the anvil assembly. The method may include securing the adapter member to a flexible tube of the anvil delivery system.

BRIEF DESCRIPTION OF THE DRAWINGS

Various embodiments of the presently disclosed anvil assembly and anvil assembly delivery system are disclosed herein with reference to the drawings wherein.

DETAILED DESCRIPTION OF EMBODIMENTS

Embodiments of the presently disclosed anvil assembly and methods for securing a head assembly of the anvil assembly will now be described in detail with reference to the drawings in which like reference numerals designate identical or corresponding elements in each of the several views. Throughout this description, the term "proximal" will refer to the portion of the instrument closest to the operator and the term "distal" will refer to the portion of the instrument furthest from the operator. In addition, the term clinician is used generally to refer to medical personnel including doctors, nurses, and support personnel.

Figure 1:
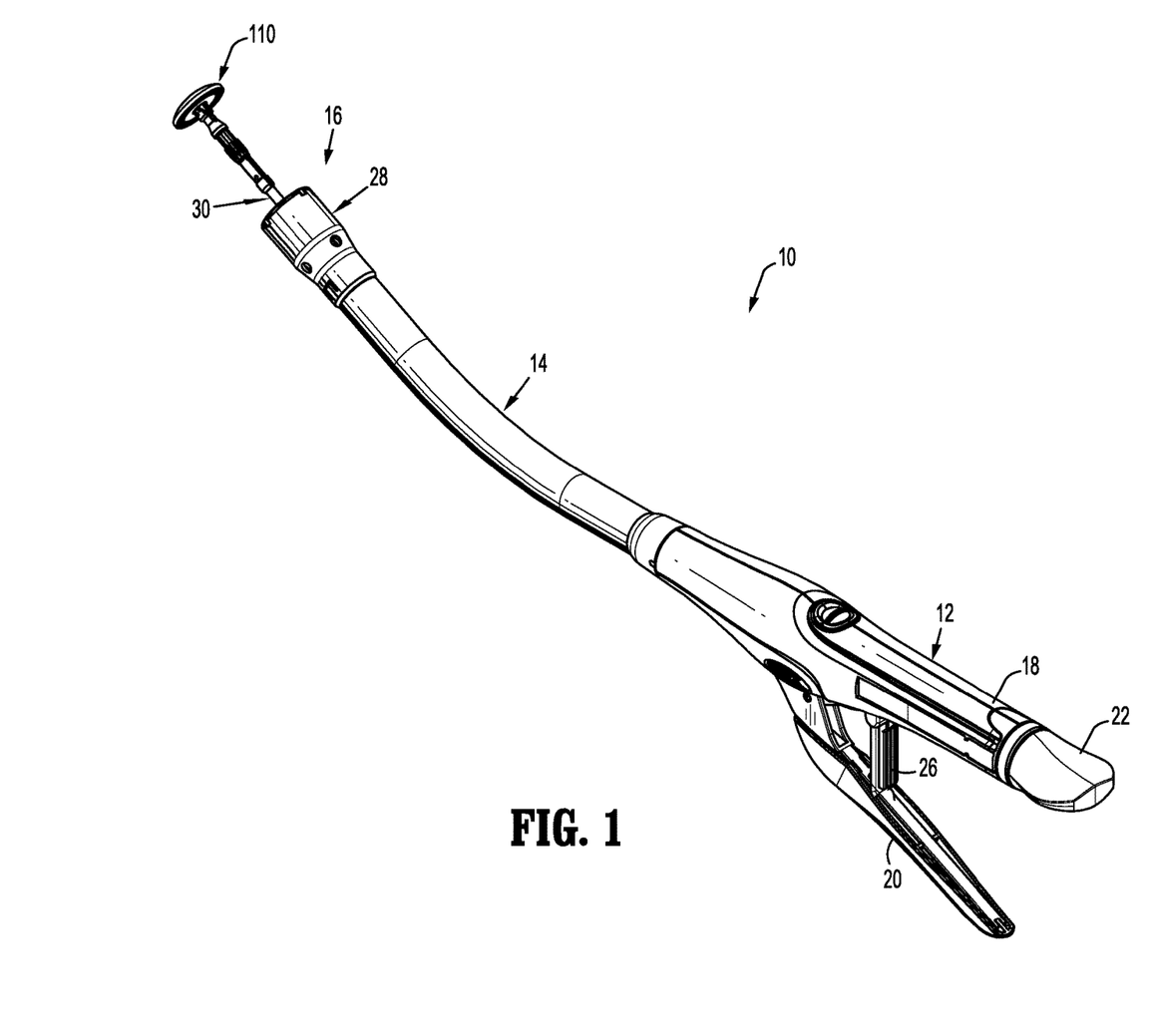
FIG. 1 is a perspective view of an anvil assembly according to an embodiment of the present disclosure releasably secured to a prior art surgical stapling instrument.

FIG. 1 illustrates an anvil assembly according an embodiment of the present disclosure shown generally as anvil assembly 110. The anvil assembly 110 is releasably secured to a prior art surgical stapling instrument 10 as known in the art. Although the anvil assembly 110 and methods of securing the anvil assembly 110 to an anvil delivery system 150 will be described with reference to the surgical stapling instrument 10 and the anvil delivery system 150 (FIG. 4), it is envisioned that the anvil assembly 110 and the methods of securing the anvil assembly 110 may be modified for use with alternative surgical stapling instruments, e.g., powered surgical instruments, and other known anvil delivery systems.

The surgical stapling instrument 10 includes a proximal handle assembly 12, an elongated central body portion 14, and a distal head portion 16. Alternately, in some surgical procedures, e.g., the treatment of hemorrhoids, it is desirable to have a substantially straight, shortened, central body portion. The length, shape and/or the diameter of the body portion 14 and the distal head portion 16 may also be varied to suit a particular surgical procedure.

The handle assembly 12 of the surgical stapling instrument 10 includes a stationary handle 18, a firing trigger 20, and a rotatable approximation knob 22. A pivotally mounted trigger lock 26 is fastened to the handle assembly 12 and is manually positioned to prevent inadvertent firing of the stapling instrument 10. The head portion 16 includes a shell assembly 28 and the anvil assembly 110. The anvil assembly 110 is releasably secured to a trocar assembly 30 that extends through the shell assembly 28 and is movable in relation to the shell assembly 28 to move the anvil assembly 110 in relation to the shell assembly 28 between spaced and approximated positions. For a detailed discussion of an exemplary surgical stapling instrument, please refer to commonly owned U.S. Pat. No. 7,364,060 to Milliman, the content of which is incorporated herein by reference in its entirety.

Figure 2:
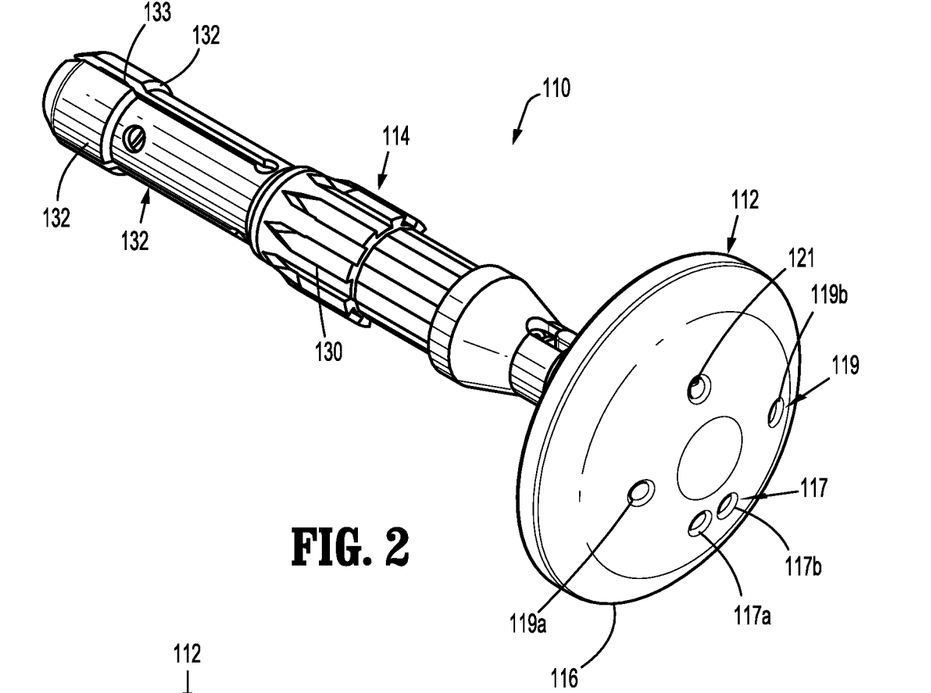
FIG. 2 is a side perspective view of the anvil assembly of FIG. 1 from the distal end.
Figure 3:
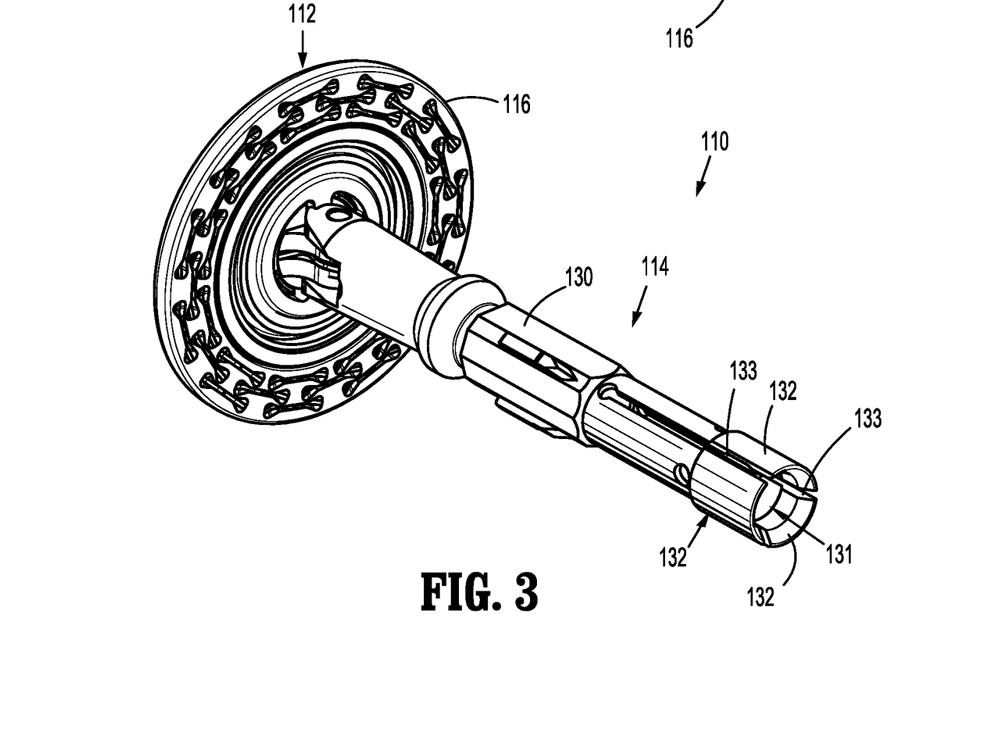
FIG. 3 is a side perspective view of the anvil assembly shown in FIGS. 1 and 2 from a proximal end.

With reference now to FIGS. 2 and 3, the anvil assembly 110 of the surgical stapling instrument 10 includes a head assembly 112 and a center rod assembly 114. The head assembly 112 is pivotally secured to the center rod assembly 114 and is movable between a first tilted position (FIG. 6) and an operative position (FIG. 1). In some embodiments, the head assembly 112 is also movable between the operative position (FIG. 1) and a second tilted position (not shown). The structure and operation of the anvil assembly 110 will only be described to the extent necessary to fully disclose aspects of the present disclosure. For a detailed description of an exemplary anvil assembly, please refer to commonly owned U.S. Pat. No. 9,554,802, the content of which is incorporated by reference herein in its entirety.

The head assembly 112 of the anvil assembly 110 includes a housing 116. The housing 116 of the head assembly 112 defines a first pair of openings 117, including first and second openings 117a, 117b, a second pair of openings 119, including first and second openings 119a, 119b, and a single opening 121. As described in further detail below, according to an embodiment of a tie-down method of the present disclosure, the first pair of openings 117 and the single opening 121 are positioned on the housing 116 of the head assembly 112 to receive a retaining suture "S1" (FIG. 6). A retrieval suture "S2" (FIG. 5) may be received through the second pair of openings 119, and/or may be received along with the retaining suture "S1" through the first pair of openings 117.

The center rod assembly 114 of the anvil assembly 110 includes a center rod 130 having distal portion and a proximal portion. The head assembly 112 is pivotally secured to the distal portion of the center rod 130. The proximal portion of the center rod 130 includes a plurality of the flexible arms 132 that define a bore 131. Slots 133 are formed between each of the plurality of flexible arms 132. As will be described in further detail below, the bore 131 (FIG. 3) defined by the plurality of flexible arms 132 receives an adapter member 162 (FIG. 4) of the anvil delivery system 150 (FIG. 4), and the slot 133 receives a longitudinal guide feature 166 of the adapter member 162 to facilitate alignment of the adapter member 162 with the head assembly 112 of the anvil assembly 110.

Figure 4:
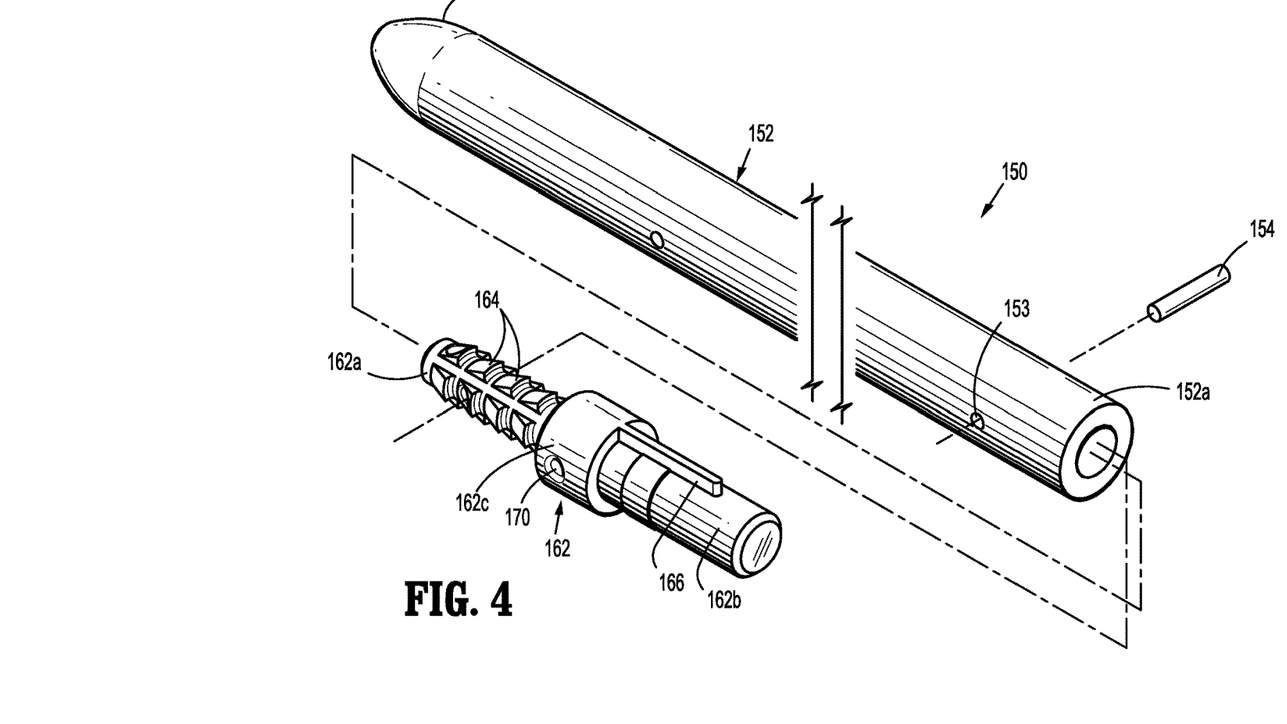
FIG. 4 is an exploded side perspective view of an anvil delivery system for delivery of the anvil assembly shown in FIGS. 1-3 with parts separated.
Figure 5:
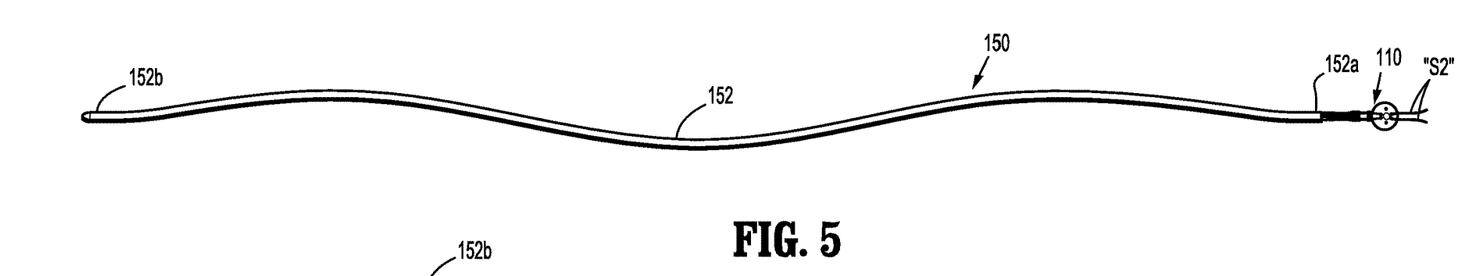
FIG. 5 is a top view of the anvil assembly shown FIGS. 1-3 secured to the anvil delivery system shown in FIG. 4.
Figure 6:
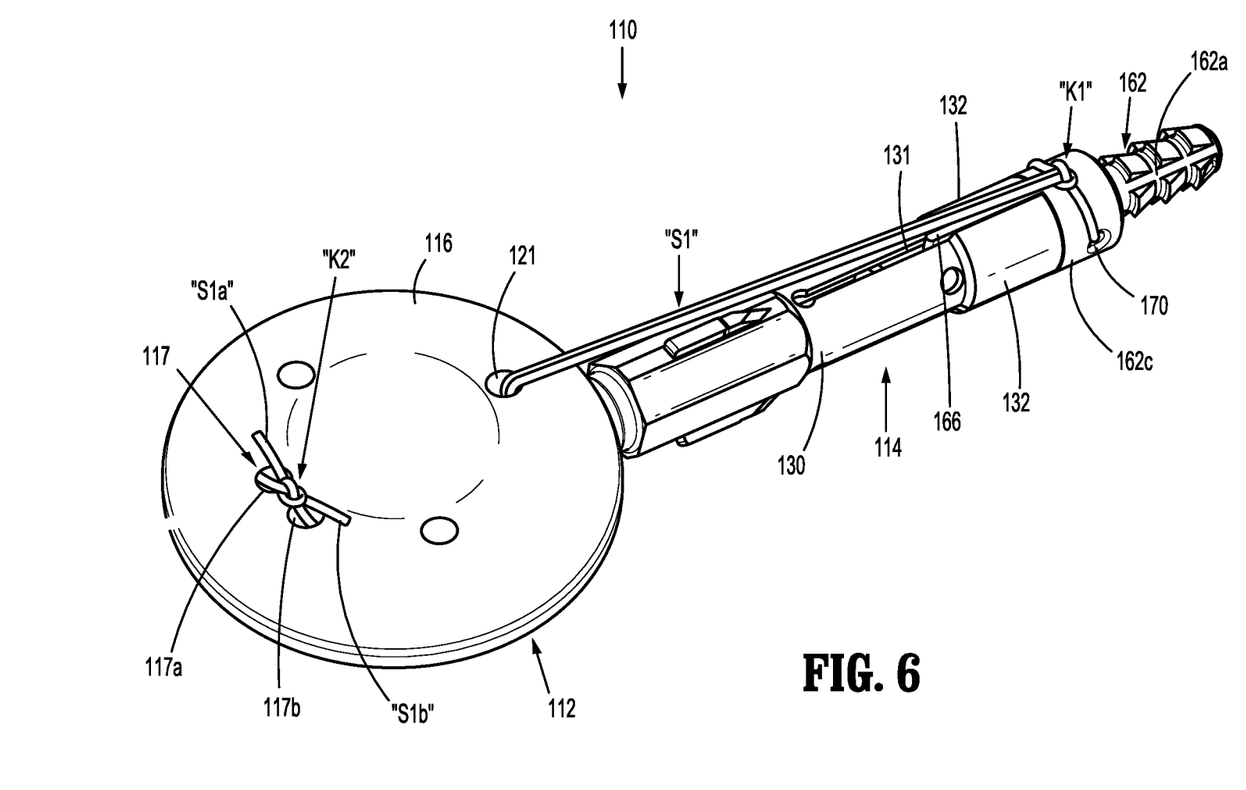
FIG. 6 is a side perspective view of the anvil assembly of FIGS. 1-3 with a head assembly of the anvil assembly tied-down in a first tilted position in accordance with a method of the present disclosure.

With reference now to FIGS. 4 and 5, the anvil delivery system 150 is configured for trans-oral insertion of the anvil assembly 110 into a patient (not shown). The anvil delivery system 150 will only be described to the extent necessary to fully disclose the aspects of the present disclosure. For a detailed description of an exemplary anvil delivery system, please refer to commonly owned U.S. Pat. No. 9,861,367 ("the '367 patent") and U.S. Pat. App. Pub. No. 2017/0000475 ("the '475 publication"), the contents of which are incorporated herein by reference in their entireties.

The anvil delivery system 150 includes a flexible tube or guide member 152 and an adapter member 162. The flexible tube 152 includes a first or open end 152a for receiving and supporting the adapter member 162 and a second or closed end 152b configured for trans-oral receipt in a patient. The open end 152a of the flexible tube 152 of the anvil delivery system 150 may include a transverse through bore 153 for receiving a locking pin 154 to secure the adapter member to 162 to the flexible tube 152.

The adapter member 162 includes a first end 162a configured to be received within the open end 152a of the flexible tube 152, and a second end 162b configured to be received with in the bore 131 formed in the second end of the center rod 130 (FIG. 3) of the anvil assembly 110. The second end 162b of the adapter member 162 includes a longitudinal guide feature 166 configured to be received in one of the slots 133 formed between the plurality of flexible arms 132 of the center rod 130 of the anvil assembly 110. A central hub portion 162c of the adapter member 162 also defines a transverse through bore 170. As will be described in detail below, the through bore 170 receives the retaining suture "S1" to facilitate tying-down of the head assembly 112 of the anvil assembly 110.

Turning to FIG. 6, the anvil assembly 110 is shown secured to the adapter member 162 of the anvil delivery system 150. The head assembly 112 of the anvil assembly 110 is maintained in the first tilted position with the retaining suture "S1" tied to the anvil assembly 110 in accordance with a method of the present disclosure. The method of tying the head assembly 112 of the anvil assembly 110 with the retaining suture "S1" will be described with reference to FIGS. 7-11.

Figure 7:
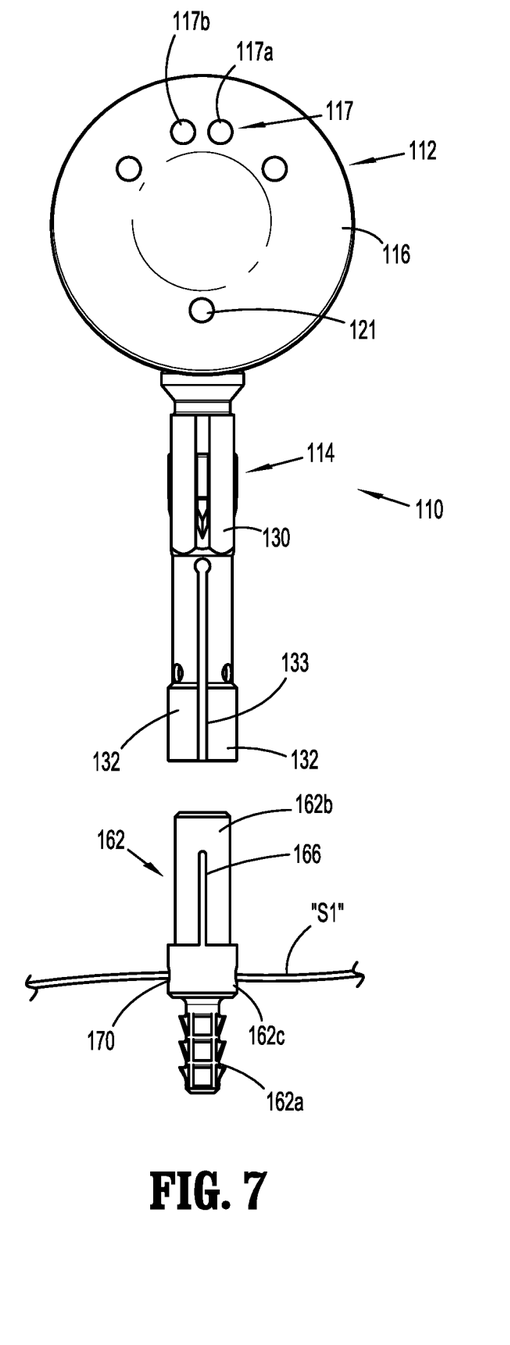
FIG. 7 is a first side view of the anvil assembly shown in FIGS. 1-3 and an adapter member of the anvil delivery system shown in FIG. 4 with a retaining suture received through the adapter member prior to the adapter member being secured to the anvil assembly.

Referring initially to FIG. 7, the retaining suture "S1" for securing the head assembly 112 of the anvil assembly 110 in a tilted position is received through the through bore 170 in the central hub portion 162c of the adapter member 162 of the anvil delivery system 150. Although shown with the adapter member 162 of the anvil delivery system 150 separate from the anvil assembly 110, it is envisioned that the adapter member 162 may be secured to the anvil assembly 110 prior to receiving the retaining suture "S1" through the through bore 170 in the adapter member 162.

Figure 8:
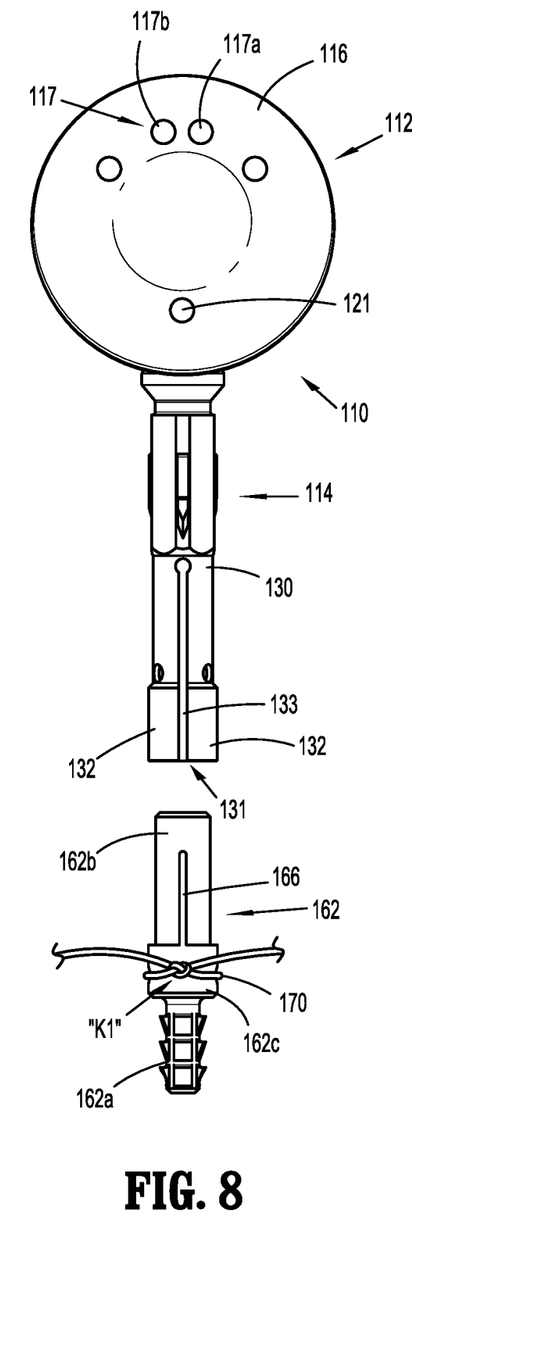
FIG. 8 is a first side view of the anvil assembly and the adapter member of the anvil delivery system shown in FIG. 7 with the retaining suture tied about adapter member and prior to the adapter member being secured to the anvil assembly.

Turning to FIG. 8, a first knot "K1" is tied in the retaining suture "S1" about the central hub portion 162c of the adapter member 162 of the anvil delivery system 150. The first knot "K1" in the retaining suture "S1" is tied in alignment with the longitudinal guide feature 166 of the adapter member 162 of the anvil delivery system 150.

Figures 9, 10, 11:
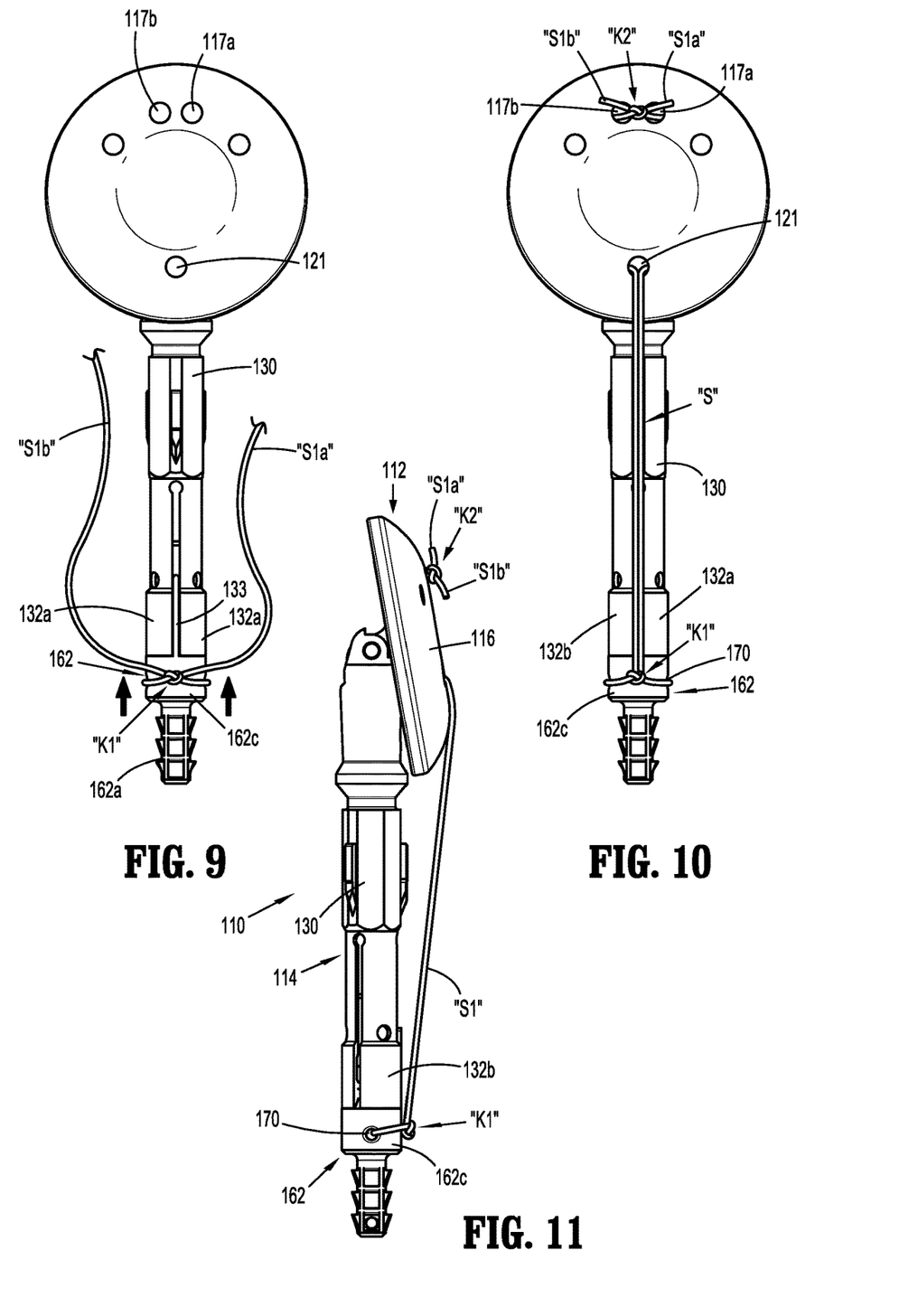
FIG. 9 is a first side view of the anvil assembly, the adapter member, and retaining suture shown in FIGS. 7 and 8 with the retaining suture tied about the adapter member and the adapter member secured to the anvil assembly.
FIG. 10 is a first side view of the anvil assembly, the adapter member, and retaining suture shown in FIGS. 7-9 with the retaining suture received through and secured to the head assembly of the anvil assembly and the head assembly tied in a first tilted position.
FIG. 11 is a second side view of the anvil assembly, the adapter member, and the retaining suture as shown in FIG. 10 with the head assembly tied in the first tilted position.

With reference now to FIG. 9, after the suture "S1" is tied to the adapter member 162, the second end 162b of the adapter member 162 is positioned within the bore 131 defined by the plurality of flexible arms 132 of the center rod 130 of the center rod assembly 114 such that the longitudinal guide feature 166 of the adapter member 162 is received within the slot 133 formed between the flexible arms 132 of the center rod 130 that is aligned with the single opening 121 in the housing 116 of the head assembly 112. Receipt of the longitudinal guide feature 166 within the slot 133 that is aligned with the single opening 121 aligns the first knot "K1" in the retaining suture "S1" with the single opening 121 in the housing 116 of the head assembly 112 of the anvil assembly 110.

Turning now to FIGS. 10 and 11, a first end "S1a" and a second end "S1b" of the retaining suture "S1" are then both received through the single opening 121 in the housing 116 of the head assembly 112 of the anvil assembly 110. Next, the first end "S1a" of the retaining suture "S1" is received through the first opening 117a of the first pair of openings 117 and the second end "S1b" of the retaining suture "S1" is received through the second opening 117b of the first pair of openings 117. The head assembly 112 is moved to the first tilted position against the bias of a spring (not shown) positioned in the distal portion of the center rod 130. The first and second ends "S1a", "S1b" of the retaining suture "S1" are then tied together to form a second knot "K2" in the retaining suture "S1". The second knot "K2" is tied such that the retaining suture "S1" maintains the head assembly 112 of the anvil assembly 110 in the first tilted position.

As seen in FIG. 10, the lengths of the retaining suture "S1" that extend between the adapter member 162 of the anvil delivery system 150 and the head assembly 112 of the anvil assembly 110 extend parallel to one another and are in close proximity to one another, e.g., in contact with one another. By maintaining both lengths of the retaining suture "S1" in close proximity to one another, both lengths of the retaining suture "S1" may be cut by a clinician with a cutting device at the same time, with one snip, to release the head assembly 112 of the anvil assembly 110. Release of the head assembly 112 of the anvil assembly 110 permits the head assembly 114 to pivot to the operative position. Positioning the lengths of suture in close proximity to each other simplifies the procedure for releasing the head assembly from the tilted position to minimize the time required to complete the cutting and reduces the likelihood of creating loose suture remnants that may be left within a body cavity.

Once the head assembly 112 of the anvil assembly 110 is secured in the first tilted position, the adapter assembly 162 of the anvil delivery system 150 is secured to the flexible tube 152 of the anvil delivery system 150 and the surgical stapling procedure is completed as described in the '367 patent and/or the '475 publication.

Persons skilled in the art will understand that the instruments and methods specifically described herein and illustrated in the accompanying drawings are non-limiting exemplary embodiments. It is envisioned that the elements and features illustrated or described in connection with one exemplary embodiment may be combined with the elements and features of another without departing from the scope of the present disclosure. As well, one skilled in the art will appreciate further features and advantages of the disclosure based on the above-described embodiments. Accordingly, the disclosure is not to be limited by what has been particularly shown and described, except as indicated by the appended claims.

What is claimed is:

1. An anvil delivery system comprising:
   a delivery assembly including an adapter member, the adapter member defining a through bore;
   an anvil assembly including:
      a center rod assembly selectively securable to the adapter member; and
      a head assembly pivotally secured to the center rod assembly, the head assembly being pivotable between a first tilted position and an operative position, the head assembly including a housing defining at least a first single opening; and
   a suture for retaining the head assembly in the first tilted position, the suture having first and second end portions, wherein the suture extends through the through bore in the adapter member and includes a first knot securing the suture about the adapter member, wherein the first and second end portions of the suture are received through the first single opening in the housing.

2. The anvil delivery system of claim 1, wherein the housing further defines a pair of openings having first and second openings, the first end portion of the suture being received through the first opening of the pair of openings and the second end portion of the suture being received through the second opening of the pair of openings.

3. The anvil delivery system of claim 2, wherein the first and second end portions of the suture form a second knot external of the first and second openings.

4. The anvil delivery system of claim 3, wherein the delivery system further includes a flexible tube, the adapter assembly being secured to the flexible tube.

5. The anvil delivery system of claim 1, wherein first and second lengths of the suture extending between the adapter member and the housing are in contact with one another.

6. The anvil delivery system of claim 1, wherein first and second lengths of the suture extending between the adapter member and the housing are parallel with one another.

7. The anvil delivery system of claim 1, wherein the head assembly is movable to a second tilted position opposite the first tilted position.

8. A method of securing an anvil assembly in a first tilted position, the method comprising:
   receiving a suture through a through bore of an adapter member of an anvil delivery system;
   securing the suture to the adapter member by tying a first knot in the suture;
   passing first and second ends of the suture through an opening in a housing of a head assembly of an anvil assembly;
   passing the first end of the suture through a first opening in the housing and passing the second end of the suture through a second opening in the housing; and securing the first and second ends of the suture together by tying a second knot in the suture adjacent the first and second ends of the suture to secure the head assembly in the first tilted position.

9. The method of claim 8, further including moving the head assembly relative to a center rod assembly of the anvil assembly to the first tilted position prior to tying the second knot.

10. The method of claim 8, further including securing the adapter member to a center rod assembly of the anvil assembly.

11. The method of claim 10, further including securing the adapter member to a flexible tube of the anvil delivery system.

12. An anvil delivery system comprising:
a delivery assembly including an adapter member, the adapter member defining a through bore:
an anvil assembly including:
a center rod assembly selectively securable to the adapter member; and
a head assembly pivotally secured to the center rod assembly, the head assembly being pivotable between a first tilted position and an operative position, the head assembly including a housing defining a first opening; and
a suture for retaining the head assembly in the first tilted position, the suture having first and second end portions, wherein the suture extends through the through bore in the adapter member and includes a first knot positioned proximal of the head assembly, the first knot securing the suture about the adapter member, wherein the first and second end portions of the suture form a second knot positioned externally of the housing.

13. An anvil delivery system comprising:
a delivery assembly including an adapter member, the adapter member defining a through bore;
an anvil assembly including:
a center rod assembly selectively securable to the adapter member; and
a head assembly pivotally secured to the center rod assembly, the head assembly being pivotable between a first tilted position and an operative position, the head assembly including a housing defining a first opening; and
a suture for retaining the head assembly in the first tilted position, the suture having first and second end portions, wherein the suture extends through the through bore in the adapter member and includes a first knot positioned proximal of the head assembly, the first knot securing the suture about the adapter member.

14. The anvil delivery system of claim 13, wherein the housing further defines a pair of openings including a first opening and a second opening, the first end portion of the suture being received through the first opening of the pair of openings and the second end portion of the suture being received through the second opening of the pair of openings.

15. The anvil delivery system of claim 13, wherein first and second lengths of the suture extending between the adapter member and the housing are in contact with one another.

16. The anvil delivery system of claim 15, wherein first and second lengths of the suture extending between the adapter member and the housing are parallel with one another.

17. The anvil delivery system of claim 13, wherein the delivery assembly further includes a flexible tube, the adapter assembly being secured to the flexible tube.

18. The anvil delivery system of claim 13, wherein the head assembly is pivotable from the operative position to a second tilted position opposite the first tilted position.

* * * * *